United States Patent
Carlo, III et al.

(10) Patent No.: US 12,201,323 B2
(45) Date of Patent: Jan. 21, 2025

(54) APPARATUSES AND METHODS FOR CORRECTING BONE DEFORMITIES

(71) Applicant: WRIGHT MEDICAL TECHNOLOGY, INC., Memphis, TN (US)

(72) Inventors: Robert Michael Carlo, III, Marion, AR (US); George Matthew Awtrey, Bartlett, TN (US); Daniel Edward Free, Arlington, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 698 days.

(21) Appl. No.: 17/415,295

(22) PCT Filed: Feb. 27, 2020

(86) PCT No.: PCT/US2020/020073
§ 371 (c)(1),
(2) Date: Jun. 17, 2021

(87) PCT Pub. No.: WO2020/180598
PCT Pub. Date: Sep. 10, 2020

(65) Prior Publication Data
US 2022/0054171 A1     Feb. 24, 2022

Related U.S. Application Data

(60) Provisional application No. 62/813,395, filed on Mar. 4, 2019.

(51) Int. Cl.
*A61B 17/56*      (2006.01)

(52) U.S. Cl.
CPC ........ *A61B 17/56* (2013.01); *A61B 2017/565* (2013.01); *A61B 2017/567* (2013.01)

(58) Field of Classification Search
CPC .............. A61B 17/56; A61B 2017/564; A61B 2017/565; A61B 2017/58; A61B 2017/681
See application file for complete search history.

(56) References Cited

U.S. PATENT DOCUMENTS 5,843,085 A    12/1998   Graser
9,271,745 B2 *   3/2016   Lizardi .............. A61B 17/1764
(Continued)

FOREIGN PATENT DOCUMENTS

FR           3059542 A1     6/2018

OTHER PUBLICATIONS

Extended Search Report issued in connection with European Patent Application No. 20765550.7, 8 pages, Nov. 7, 2022.
(Continued)

*Primary Examiner* — Ellen C Hammond
*Assistant Examiner* — Holly Joanna Lane
(74) *Attorney, Agent, or Firm* — Duane Morris LLP

(57) ABSTRACT

An apparatus for correcting bunion deformity includes an elongated member, a first arm member extending from a first end to a second end, a second arm member, and a rotation guide. The first arm member has an arm axis and is coupled to the first end of the elongated member so that the arm axis extends in an orthogonal direction from the elongated member. The second arm member includes an attachment portion configured to translatably engage the elongated member and an extension extending in the same orthogonal direction as the first arm member. The rotation guide is coupled to the first arm member such that the rotation guide is configured to rotate with respect to the first arm member about a rotation axis, the rotation guide defining a bore having a longitudinal axis.

15 Claims, 17 Drawing Sheets

(56) References Cited

U.S. PATENT DOCUMENTS

| | | | |
|---|---|---|---|
| 9,622,805 B2 | 4/2017 | Santrock et al. | |
| 10,987,146 B2* | 4/2021 | Denham | A61B 17/86 |
| 11,123,120 B2* | 9/2021 | Dacosta | A61B 17/1728 |
| 2007/0239168 A1* | 10/2007 | Kuenzi | A61B 17/1728 |
| | | | 606/96 |
| 2009/0036893 A1 | 2/2009 | Kartalian et al. | |
| 2010/0121447 A1* | 5/2010 | Troger | A61F 2/0805 |
| | | | 623/13.11 |
| 2010/0217328 A1 | 8/2010 | Terrill et al. | |
| 2010/0331844 A1 | 12/2010 | Ellis et al. | |
| 2011/0077656 A1 | 3/2011 | Sand et al. | |
| 2012/0209268 A1* | 8/2012 | Overes | A61B 17/1725 |
| | | | 606/62 |
| 2013/0245701 A1 | 9/2013 | Kartalian et al. | |
| 2014/0228899 A1* | 8/2014 | Thoren | A61B 17/6483 |
| | | | 606/86 R |
| 2016/0213384 A1 | 7/2016 | Fallin et al. | |
| 2017/0020538 A1* | 1/2017 | Wong | A61B 17/1703 |
| 2017/0042598 A1 | 2/2017 | Santrock et al. | |
| 2017/0216043 A1* | 8/2017 | Surma | A61B 17/8645 |
| 2018/0185079 A1 | 7/2018 | Smith et al. | |
| 2021/0330311 A1* | 10/2021 | Denham | A61B 17/025 |
| 2022/0192685 A1* | 6/2022 | Gazonnet | A61B 17/1739 |
| 2023/0190352 A1* | 6/2023 | Coyne | A61B 17/8095 |
| | | | 606/87 |

OTHER PUBLICATIONS

International Search Report and Written Opinion for PCT/US2020/020073 issued Jun. 4, 2020.
First Office Action issued in connection with corresponding Canadian Patent Application No. 3,125,644, Sep. 11, 2023, 3 pages.

* cited by examiner

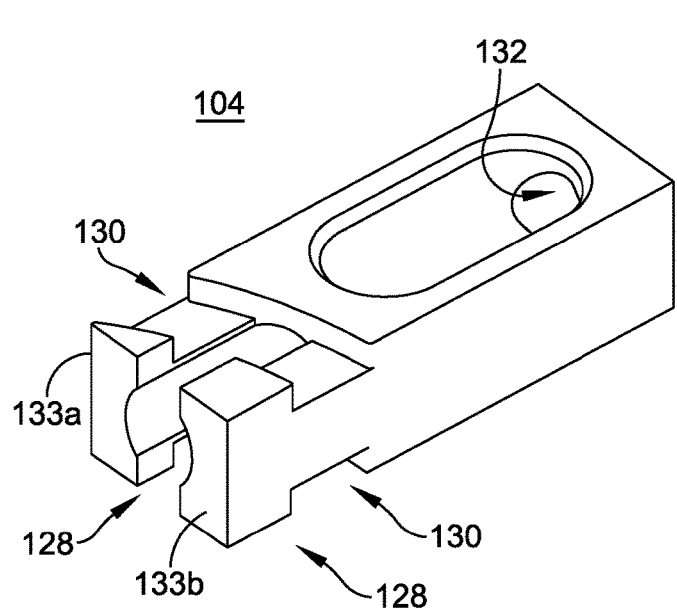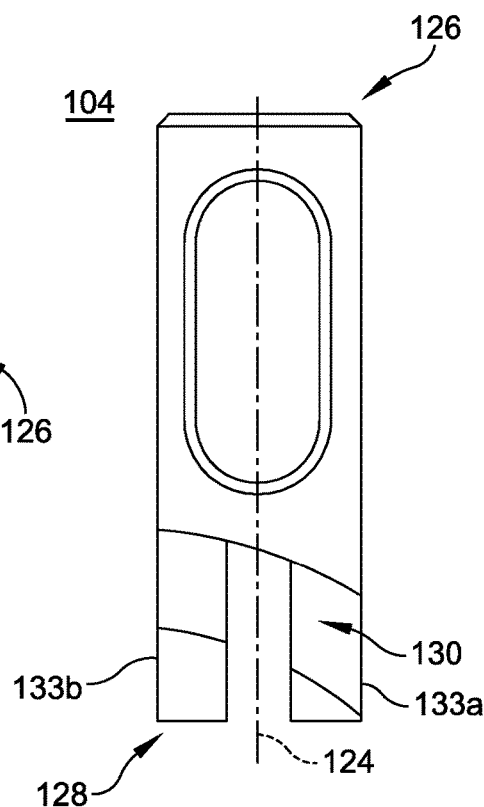
FIG. 4
FIG. 5
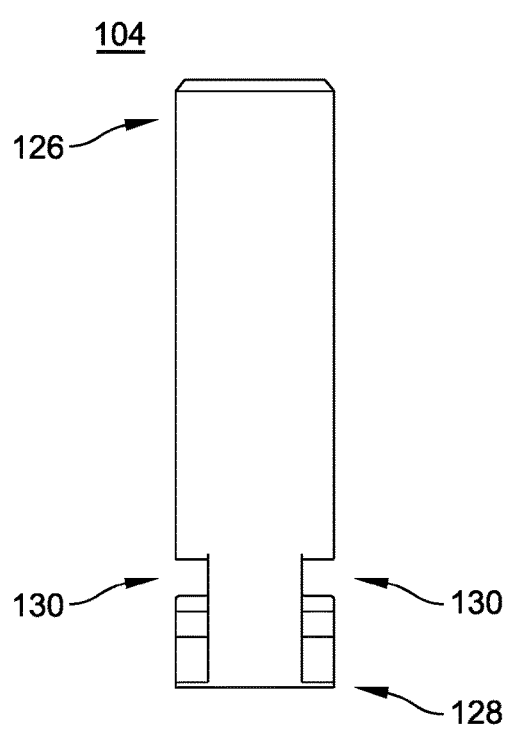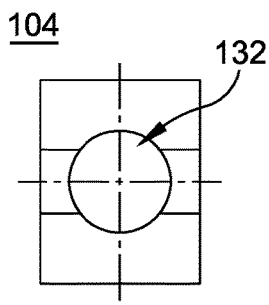
FIG. 6
FIG. 7

APPARATUSES AND METHODS FOR CORRECTING BONE DEFORMITIES

CROSS-REFERENCE TO RELATED APPLICATIONS

This application is a National Stage Application, filed under 35 U.S.C. 371, of International Patent Application No. PCT/US2020/020073, filed on Feb. 27, 2020, which claims priority to U.S. Provisional Patent Application No. 62/813,395, filed on Mar. 4, 2019, the entirety of which is hereby incorporated herein by reference the entireties of which are incorporated herein by reference.

FIELD

This disclosure relates generally to surgical tools, and more specifically to apparatuses and methods for correcting hallux valgus angle.

BACKGROUND

Hallux valgus deformities in the human foot relate to a condition in which the first (great) toe has a deviated position leaning in towards the second toe. The first metatarsal deviates towards the mid-sagittal plane, and the great toe deviates away from the mid-sagittal plane. This is often accompanied by a bump due to a swollen bursal sac or a bony anomaly on the metatarsophalangeal joint.

A variety of non-surgical methods are used to treat hallux valgus, but in cases of continued pain or visible deformity, the patient may seek a surgical correction of the condition. Surgical methods may include removing the bony enlargement of the first metatarsal, realigning the first metatarsal bone relative to the adjacent metatarsal bone, and/or straightening the great toe relative to the first metatarsal and adjacent toes.

One such method of treating hallux valgus deformities is known as a Lapidus procedure. In a Lapidus procedure, the first metatarsal is realigned and then the first tarsal-metatarsal joint is fused to decrease the movement of the joint. This straightens the first metatarsal and toe to reduce or eliminate the hallux valgus deformity.

SUMMARY

In one aspect, an apparatus for correcting bunion deformity includes an elongated member, a first arm member, a second arm member, and a rotation guide. The elongated member extends from a first end to a second end. The first arm member has an arm axis and is coupled to the first end of the elongated member and extends in an orthogonal direction from the elongated member so that the arm axis extends in the orthogonal direction. The second arm member is configured to engage the elongated member such that the second arm member can translate along the elongated member between the first and second ends of the elongated member. The second arm member includes an attachment portion configured to translatably engage the elongated member and an extension extending from the attachment portion in the same orthogonal direction as the first arm member and a distal end of the extension is configured to engage a bone during use. The rotation guide is coupled to the first arm member such that the rotation guide is configured to rotate with respect to the first arm member, the rotation guide defining a bore having a longitudinal axis and configured to receive a k-wire along the bore's longitudinal axis. The rotation of the rotation guide with respect to the first arm member causes the longitudinal axis to rotate about a rotation axis.

In another aspect, an apparatus for correcting bunion deformity includes an elongated member, a first arm member, a second arm member, a rotation guide, and a locking mechanism. The elongated member extends from a first end to a second end. The first arm member has an arm axis and is coupled to the first end of the elongated member and extends in an orthogonal direction from the elongated member so that the arm axis extends in the orthogonal direction. The first arm member is configured to rotate about an arm axis extending from a first end of the first arm member to a second end of the first arm member. The second arm member is configured to engage the elongated member such that the second arm member can translate along the elongated member between the first and second ends of the elongated member. The second arm member includes an attachment portion configured to translatably engage the elongated member and an extension extending from the attachment portion. The rotation guide includes an arcuate portion engaged with the first arm member such that the rotation guide is configured to rotate with respect to the first arm member about a rotation axis. The rotation guide defines a bore configured to receive a k-wire. The locking mechanism is configured to selectively restrict rotation of the first arm member about the arm axis and rotation of the rotation guide about the rotation axis.

In another aspect, a method for correcting bunion deformity includes inserting a k-wire into a first metatarsal. The method further includes engaging an engagement portion of a second arm member with a second metatarsal. The method further includes sliding a rotation guide over the k-wire such that the k-wire is disposed in a bore of the rotation guide, the rotation guide rotatably coupled to a first arm member. The method further includes inserting an elongated member through an attachment portion of the second arm member, the elongated member having a first end and a second end, wherein the first arm member is coupled to the first end. The method further includes reducing a first distance between the first arm member and the second arm member to reduce a second distance between the first metatarsal and the second metatarsal. The method further includes rotating the rotation guide with respect to the first arm member to rotate the first metatarsal about a longitudinal axis of the first metatarsal.

In another aspect, an apparatus for correcting bunion deformity includes an elongated member, a first arm member, a second arm member, and a rotation guide. The elongated member extends from a first end to a second end. The first arm member is coupled to the first end of the elongated member and extends from the elongated member. The first arm member includes an arcuate portion defining a slot and at least one contact arm configured to contact a first bone during use. A track is defined between the arcuate portion and the at least one contact arm. The second arm member is configured to engage the elongated member such that the second arm member can translate along the elongated member between the first and second ends of the elongated member. The second arm member includes an attachment portion configured to translatably engage the elongated member and an extension extending from the attachment portion. A distal end of the extension is configured to engage a second bone during use. The rotation guide is coupled to the arcuate portion of the first arm member and is at least partially disposed in the track defined by the arcuate portion the at least one contact arm such that the rotation guide is configured to rotate with respect to the arcuate portion. The rotation guide defines a bore having a longitudinal axis and configured to receive a k-wire along the bore's longitudinal axis. Rotation of the rotation guide with respect to the first arm member causes the longitudinal axis to rotate about a rotation axis. The rotation guide is spaced apart from the first bone during use.

BRIEF DESCRIPTION OF THE DRAWINGS

These and other features and advantages of the apparatuses and methods described herein will be more fully disclosed in, or rendered obvious by, the following detailed description of the preferred embodiments, which is to be considered together with the accompanying drawings wherein like numbers refer to like parts.

FIG. 4 shows a perspective view of a first arm member of the apparatus of FIG. 1.

FIG. 5 shows a front view of the first arm member of FIG. 4.

FIG. 6 shows a side view of the first arm member of FIG. 4.

FIG. 7 shows a top view of the first arm member of FIG. 4.

DETAILED DESCRIPTION

Figure 1:
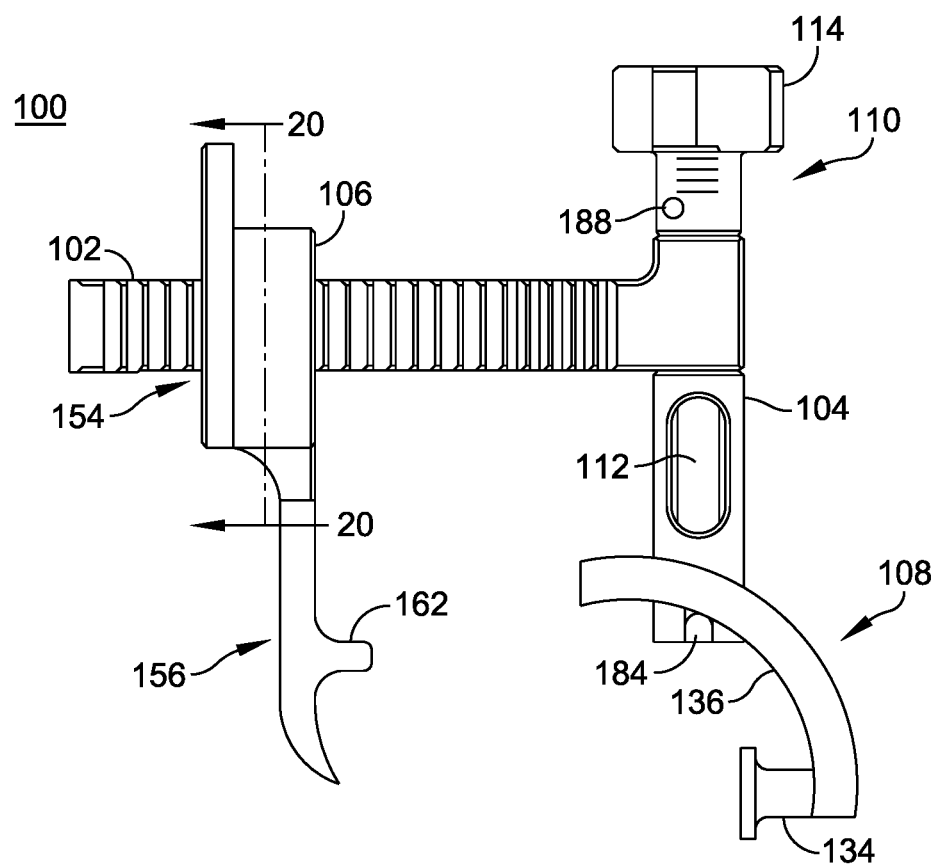
FIG. 1 shows a front view of an apparatus for correcting bone deformities, according to one embodiment.

This description of preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

The apparatuses described herein are configured for use in correction of bone deformities. Although the apparatuses can be used to correct deformities of any bone, they are particularly well-suited for use in correcting increased intermetatarsal angle between the first and second metatarsals of the foot. The apparatuses can be used in what is known as a Lapidus procedure. In addition, the apparatuses can be used to rotate the first metatarsal about a longitudinal axis of the first metatarsal to further realign the anatomy of the foot.

Figure 2:
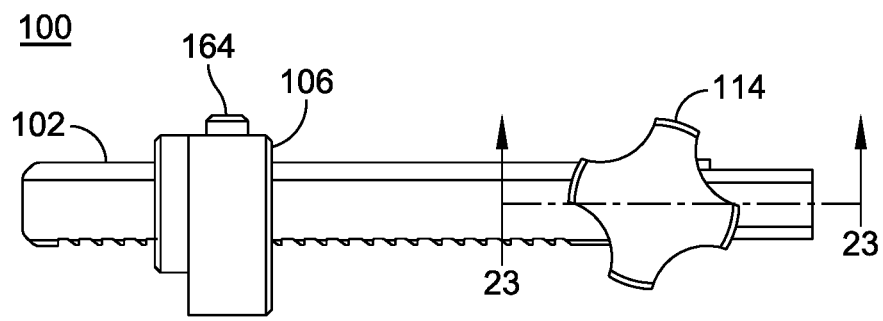
FIG. 2 shows a top view of the apparatus of FIG. 1.

In one embodiment, as shown in FIGS. 1-2, an apparatus 100 for correcting a bunion deformity includes an elongated member 102, a first arm member 104, a second arm member 106, and a rotation guide 108. The apparatus 100 also includes a locking mechanism 110 that includes a locking post 112 and a knob 114.

Figure 3:
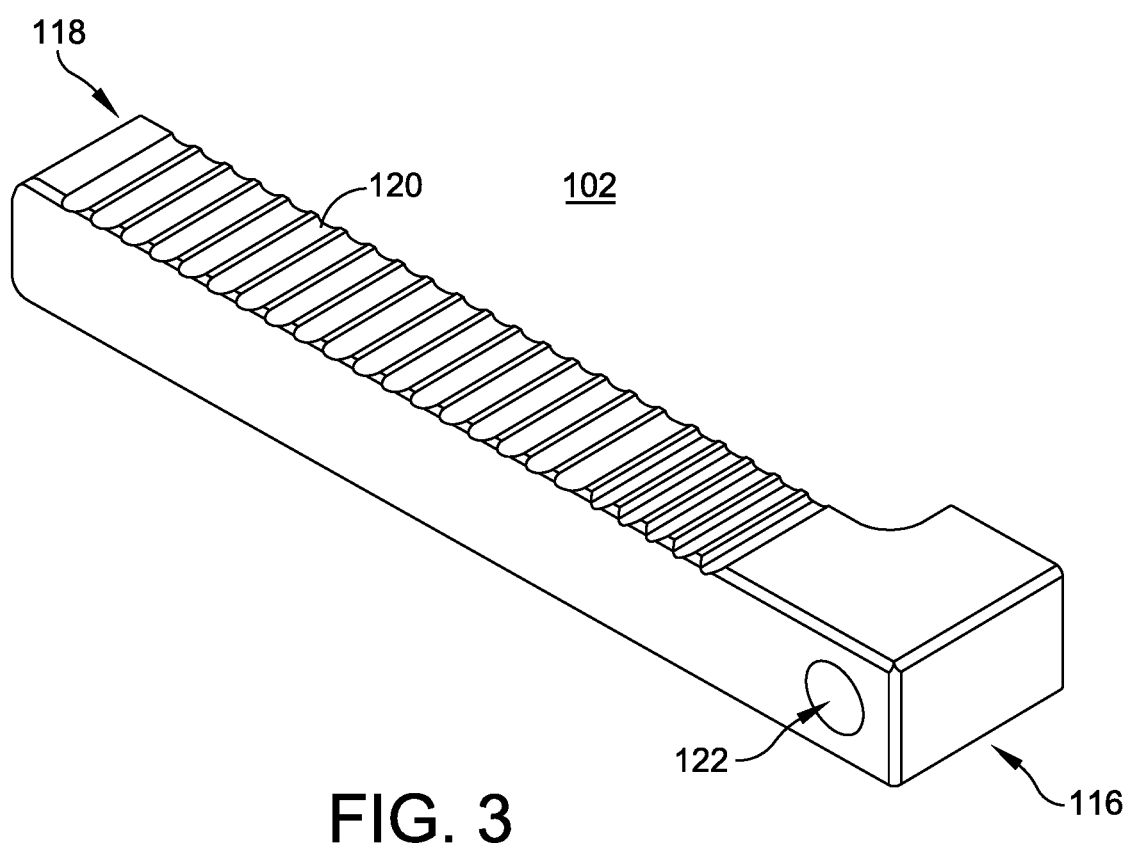
FIG. 3 shows a perspective view of an elongated member of the apparatus of FIG.

As shown in FIG. 3, the elongated member 102 extends from a first end 116 to a second end 118. The elongated member 102 includes a plurality of ratchet teeth 120. As will be described further herein, the second arm member 106 is configured to selectively engage the plurality of ratchet teeth 120 to restrict translation of the second arm member 106 along the elongated member 102. As shown in FIG. 3, the elongated member 102 includes a bore 122 at its first end 116.

The first arm member 104 is shown in more detail in FIGS. 4-7. As shown in FIG. 5, the first arm member 104 has an arm axis 124 extending from a first end 126 of the first arm member 104 to a second end 128 of the first arm member 104. As shown in FIG. 1, the first arm member 104 is coupled to the first end 116 of the elongated member 102 with the first end 126 of the first arm member 104 adjacent the elongated member 102. When coupled to the elongated member 102, the first arm member 104 extends away from the elongated member 102 so that the arm axis 124 of the first arm member 104 extends away from the elongated member 102 (e.g., in an orthogonal direction relative to the length of the elongated member 102). As shown in FIGS. 4-6, the first arm member 104 includes grooves 130 on the external surface of the first arm member 104. As will be described further herein, in use, the rotation guide 108 rides in the external grooves 130 and the external grooves 130 constrain and guide the rotation of the rotation guide 108. As shown best in FIG. 7, the first arm member 104 also includes a bore 132 extending therethrough. As will be described further herein, the bore 132 is configured to allow passage of the locking post 112, as shown in FIG. 1. The second end 128 of the first arm member 104 includes two prongs 133a, 133b separated by a gap. The grooves 130 may be defined in the prongs 133a, 133b.

Figure 8:
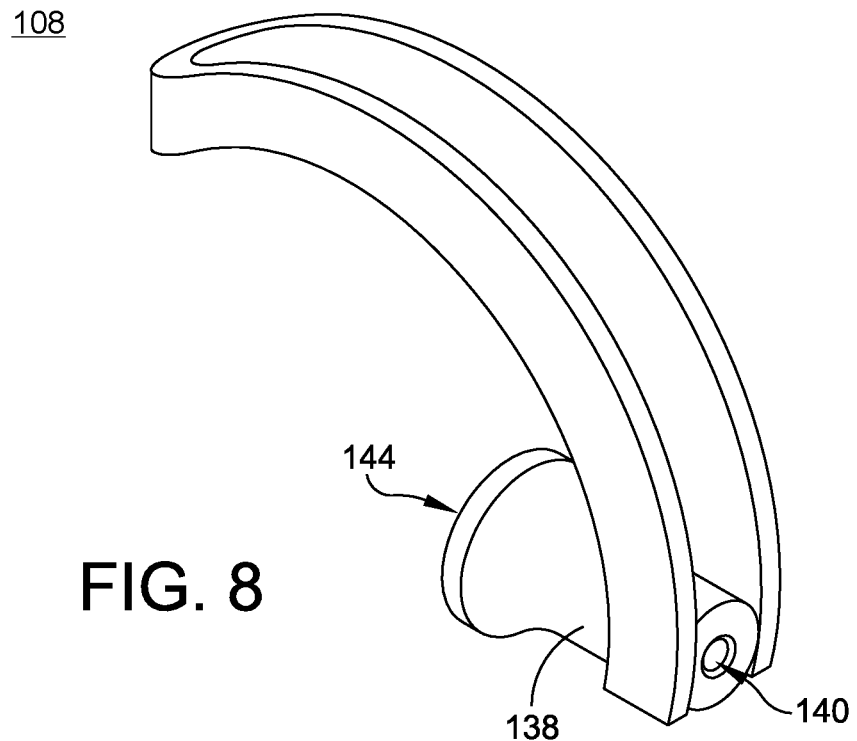
FIG. 8 shows a perspective view of a rotation guide of the apparatus of FIG. 1.
Figure 9:
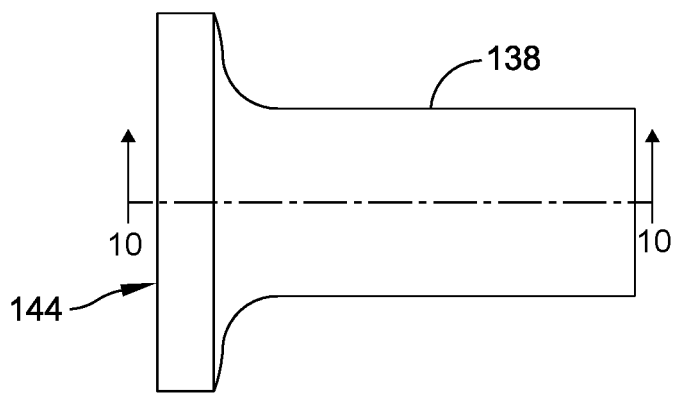
FIG. 9 shows a side view of a wire retainer of the rotation guide of FIG. 8.
Figure 10:
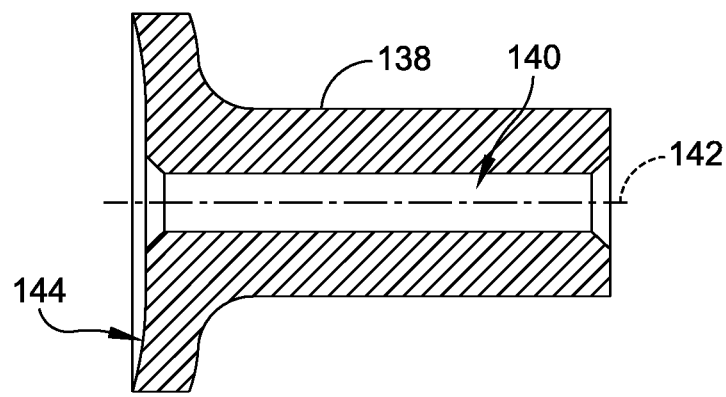
FIG. 10 shows a side cross-sectional view of the wire retainer of FIG. 9.

As shown in FIG. 8, the rotation guide 108 includes a wire retainer 134 and an arcuate portion 136. As shown in FIGS. 9 and 10, the wire retainer 134 includes a body 138 and a bore 140 extending through the body 138. The bore 140 is sized and configured to receive a k-wire therein. The bore 140 can be any appropriate diameter to receive the appropriately sized k-wire. The bore 140 defines a longitudinal axis 142. The wire retainer 134 also includes a bone engagement face 144. The bone engagement face 144 can be shaped to conform to the bone. For example, the bone engagement face 144 can be concave, as shown in FIG. 10. The bone engagement face 144 is at an end of the body 138 that has a larger diameter than other portions of the body 138.

Figure 11:
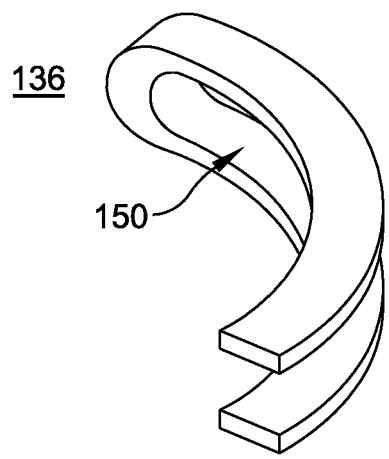
FIG. 11 shows a perspective view of an arcuate portion of the rotation guide of FIG. 8.
Figure 12:
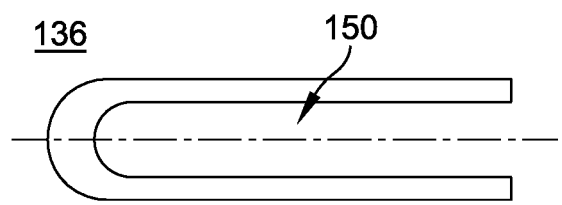
FIG. 12 shows a top view of the arcuate portion of FIG. 11.
Figure 13:
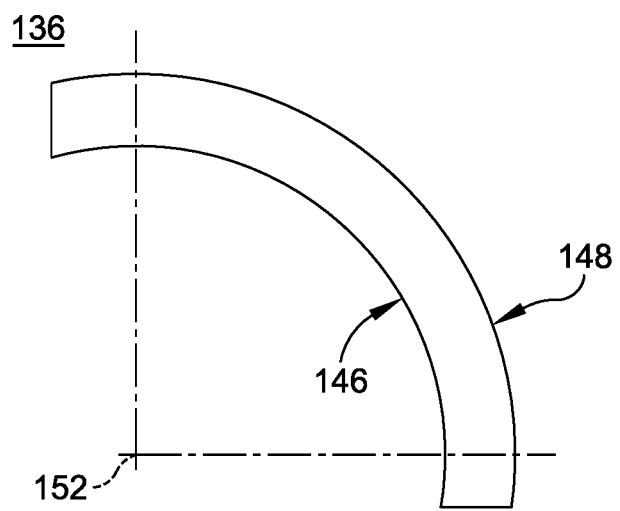
FIG. 13 shows a front view of the arcuate portion of FIG. 11.
Figure 35B:
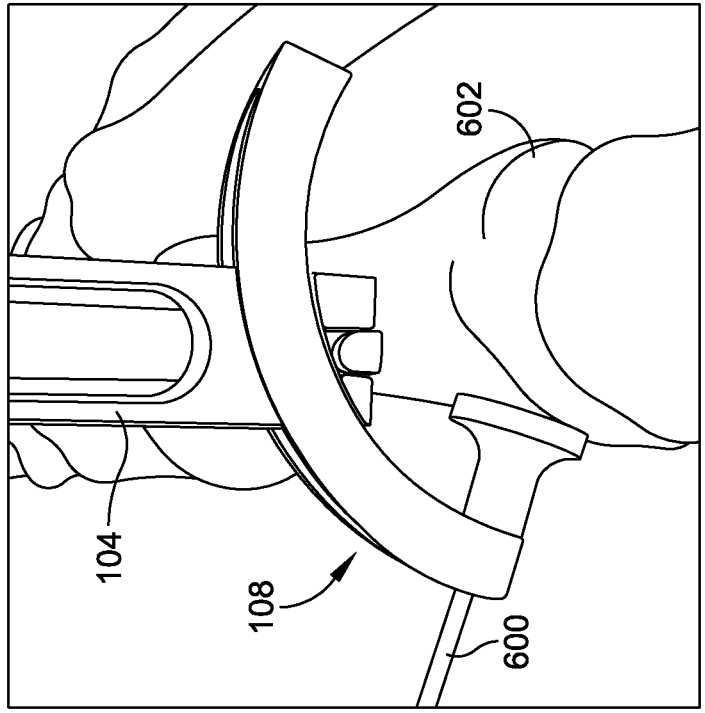
FIGS. 35A and 35B shows the apparatus of FIG. 1 in a fifth step of use in which the first metatarsal is rotated about its longitudinal axis.
Figure 35A:
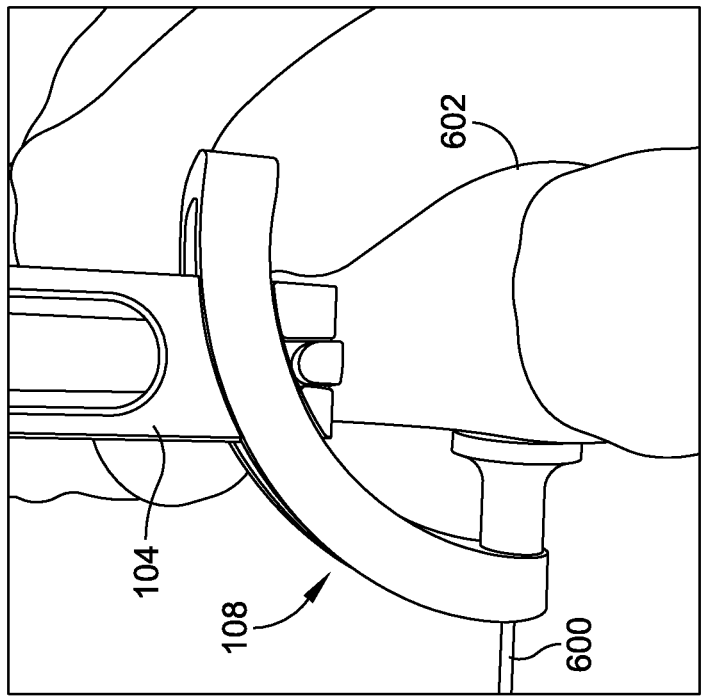

The arcuate portion 136 is shown in more detail in FIGS. 11-13. The arcuate portion 136 includes an inner face 146, an outer face 148, and a slot 150 extending therebetween. As shown in FIGS. 35A and 35B, the first arm member 104 is slidably received in the slot 150 for enabling rotation of the arcuate portion 136 with respect to the first arm member 104. Alternatively, or additionally, the first arm member 104 can move along the arcuate portion 136 within the slot 150. In at least one embodiment, as shown in FIG. 11, the slot 150 is open at one end. In such embodiments, as described in more detail below, the wire retainer 134 is coupled to the arcuate portion 136 at the open end of the slot 150. The inner face 146 and the outer face 148 are curved and each define a portion of a cylinder. A rotation axis 152 is defined at the center of the cylinder. The radius of the inner face 146 and outer face 148 can be chosen to provide the appropriate spacing and clearance during use. For example, in one embodiment, the outer face 148 has a radius of between 0.5 inches and 1.5 inches. In another embodiment, the inner face 146 has a radius of approximately 1.0 inches.

As shown in FIG. 8, the wire retainer 134 is coupled to the arcuate portion 136 at the open end of the slot 150 such that the longitudinal axis 142 of the bore 140 intersects the rotation axis 152 of the arcuate portion 136. In at least one embodiment, the longitudinal axis 142 is orthogonal to the rotation axis 152. Further, in one embodiment, when assembled, one or both of the longitudinal axis 142 and the rotation axis 152 intersect the arm axis 124. The wire retainer 134 can be coupled to the arcuate portion 136 by any appropriate method. For example, the wire retainer 134 can be coupled to the arcuate portion 136 by welding, bonding, or any other appropriate method. In an alternative embodiment, the wire retainer 134 and the arcuate portion 136 are integrally formed, for example by casting, injection molding, or additive manufacturing (e.g., 3-D printing).

Figure 14:
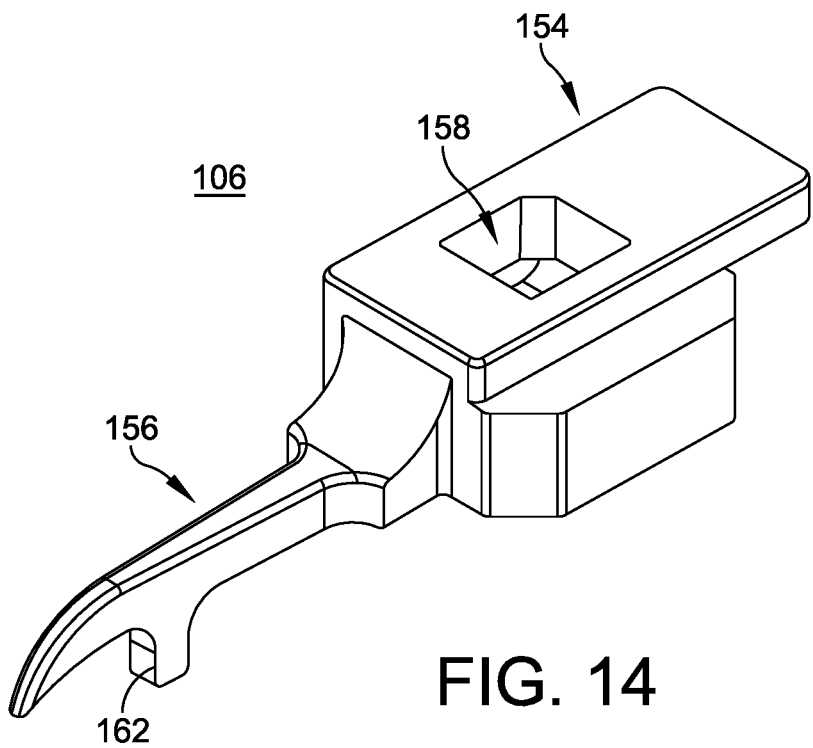
FIG. 14 shows a perspective view of a second arm member of the apparatus of FIG. 1.
Figure 15:
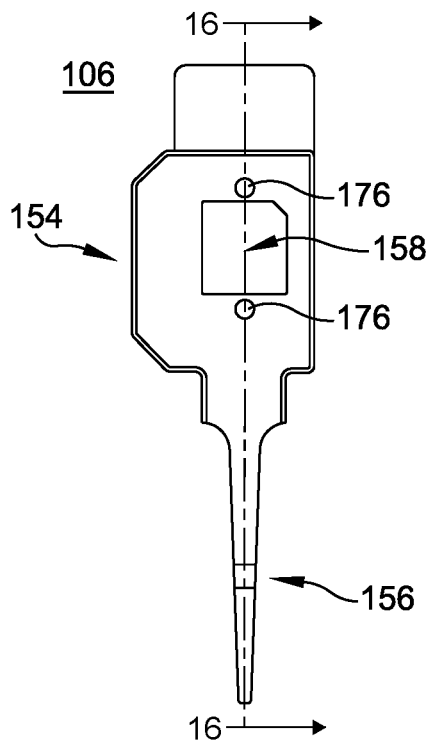
FIG. 15 shows a side view of the second arm member of FIG. 14.
Figure 16:
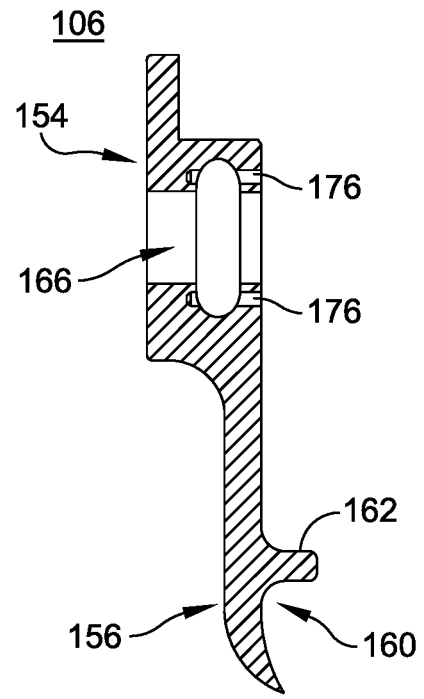
FIG. 16 shows a front cross-sectional view of the second arm member of FIG. 14.

As shown in FIGS. 14-16, the second arm member 106 includes an attachment portion 154 and an extension 156. The attachment portion 154 is configured to translatably engage the elongated member 102. In one embodiment, the attachment portion 154 includes a passage 158 configured to receive the elongated member 102. The extension 156 extends away from the elongated member 102, for example in an orthogonal direction with respect to the elongated member 102. In one embodiment, the extension 156 extends in the same orthogonal direction as the arm axis 124 of the first arm member 104 such that they are parallel. The distal end of the extension 156 (i.e., the end of the extension 156 opposite the attachment portion 154) is configured to engage a second bone during use. The extension 156 includes a concave portion 160 shaped to conform to the second bone. The concave portion 160 can have a variable radius such that the radius increases nearer the end of the extension 156. In addition, a protrusion 162 protrudes from the extension 156 such that, when the second arm member 106 is engaged with the elongated member 102, the protrusion 162 extends toward the second end 128 of the first arm member 104 (i.e., parallel to the elongated member 102). Alternatively, the protrusion 162 can extend toward the rotation axis 152. In use, the protrusion 162 is configured to contact the top of the second bone. In one embodiment, the extension 156 is tapered, as shown best in FIG. 15 such that the extension 156 comes to a point at the end farthest from the elongated member 102. The tapering and pointed configuration of the extension 156 allows it be inserted through a small incision during use.

Figure 17:
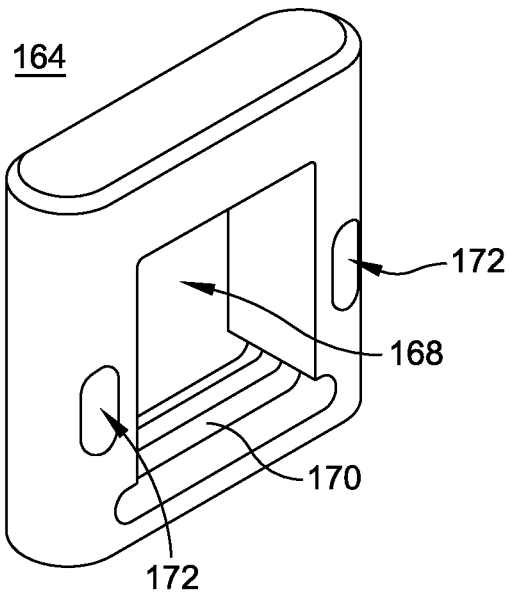
FIG. 17 shows a perspective view of a button of the apparatus of FIG. 1.
Figure 18:
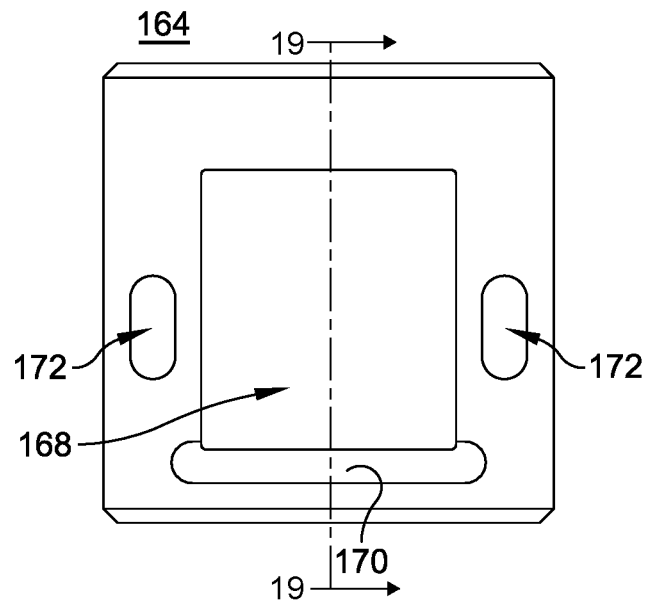
FIG. 18 shows a side view of the button of FIG. 17.
Figure 19:
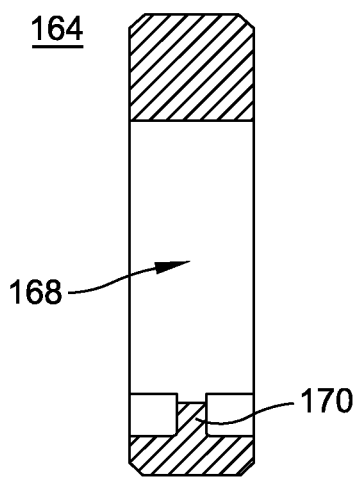
FIG. 19 shows a front cross-sectional view of the button of FIG. 17.
Figure 20:
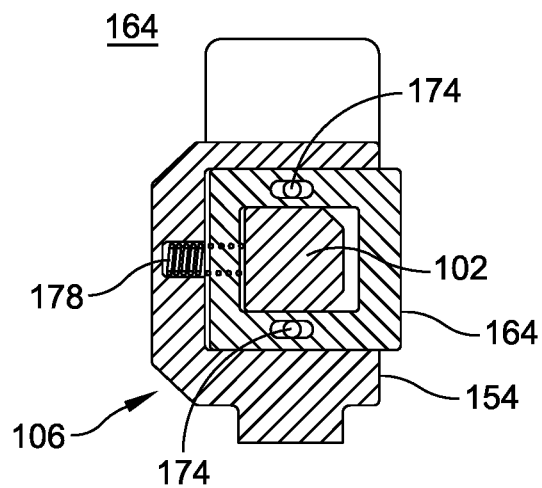
FIG. 20 shows a side cross-sectional view the apparatus of FIG. 1.

The second arm member 106 is configured to engage the plurality of ratchet teeth 120 of the elongated member 102 to control the distance between the second arm member 106 and the first arm member 104. Any appropriate means for engaging the plurality of ratchet teeth 120 can be used. In one embodiment, a button 164, shown in FIGS. 17-19, is coupled to the second arm member 106 and configured to engage the plurality of ratchet teeth 120. The button 164 is disposed in a recess 166 (shown in FIG. 16) in the attachment portion 154 of the second arm member 106. The button 164 includes a passage 168 configured to receive the elongated member 102. The button 164 also includes one or more teeth 170 adjacent the passage 168 and configured to engage one or more of the ratchet teeth 120. The button 164 also includes slots 172. As shown in FIG. 20, during assembly, pins 174 are inserted through holes 176 (shown in FIGS. 15 and 16) in the attachment portion 154 and into the slots 172. When the button 164 is depressed, the interaction of the pins 174 and the slots 172 guide translation of the button 164. In at least one embodiment, a biasing member 178, such as a coil spring, biases the button 164 to a position in which the tooth 170 is engaged with the elongated member 102.

Figure 21:
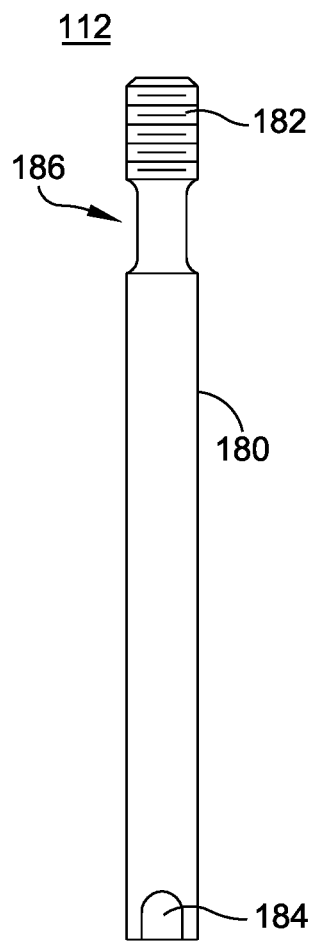
FIG. 21 shows a front view of a locking post of the apparatus of FIG. 1.
Figure 22:
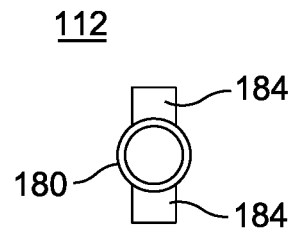
FIG. 22 shows a top view of the locking post of FIG. 21.
Figure 23:
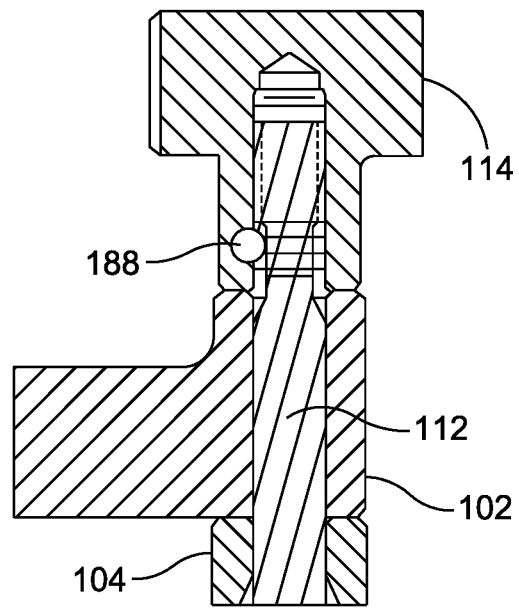
FIG. 23 shows a front cross-sectional view of the apparatus of FIG. 1.

As shown in FIG. 21, the locking post 112 includes a shaft 180 having a threaded end 182 configured to engage the knob 114. As shown in FIGS. 21 and 22, at the opposite end of the shaft 180, the locking post 112 has locking tabs 184 extending from the shaft 180. When the apparatus 100 is assembled, the locking tabs 184 are disposed in the space between the prongs 133a, 133b at the second end of the first arm member 104 (see FIGS. 4 and 5). Because the locking tabs 184 are disposed between the prongs 133a, 133b, the locking post 112 and the first arm member 104 rotate together. As will be described in more detail herein, when the knob 114 is rotated (e.g., in a clockwise or counterclockwise direction), the locking post 112 is pulled upward and the locking tabs 184 contact the arcuate portion 136 of the rotation guide 108 to restrict rotation of both the first arm member 104 and the rotation guide 108. The locking tabs 184 include a curved top surface to provide a smooth contact surface for engaging the arcuate portion 136. As shown in FIG. 21, the locking post 112 also includes a reduced diameter section 186. As shown in FIG. 23, when assembled, a retainer 188—such as a pin, set screw, or ball detent—coupled to the knob 114 is disposed in the reduced diameter section 186 to prevent inadvertent disassembly of the knob 114 and the locking post 112.

As described above, when assembled, the first arm member 104 is configured to rotate around the arm axis 124 and the rotation guide 108 is configured to rotate around the rotation axis 152. When the knob 114 is rotated to tighten the locking post 112, the locking tabs 184 contact, and apply an upward force on, the inner face 146 of the arcuate portion 136. This force causes the outer face 148 of the arcuate portion 136 to come into contact with the top of the grooves 130 of the first arm member 104. The rotation guide 108 is thereby locked in place relative to the first arm member 104 to prevent rotation about the rotation axis 152. In addition, this upward force also causes the top of the first arm member to be pressed against the elongated member 102, thereby restricting rotation of the first arm member 104 about the arm axis 124. The locking mechanism 110 can be held in this locked configuration by the engagement of the threads of the locking post 112 and knob 114. Alternatively, or additionally, additional methods of securing the locking mechanism 110 can be used.

Additional embodiments of an apparatus for correcting bunion deformities are shown in FIGS. 24-29 and 36-38. Aspects of these embodiments may be similar to those of apparatus 100 and duplicative description is not repeated herein. In these figures and the accompanying description, the leading digit of the relevant reference number has been incremented (e.g., 102, 202, 302). While the features or aspects of these additional embodiments may be similar to the description above, they need not be identical. In addition, features of the various embodiments can be combined. Furthermore, the embodiments of FIGS. 24-29 can include features or components shown or described with reference to FIGS. 1-23 and not shown in FIGS. 24-29 and vice versa.

Figure 24:
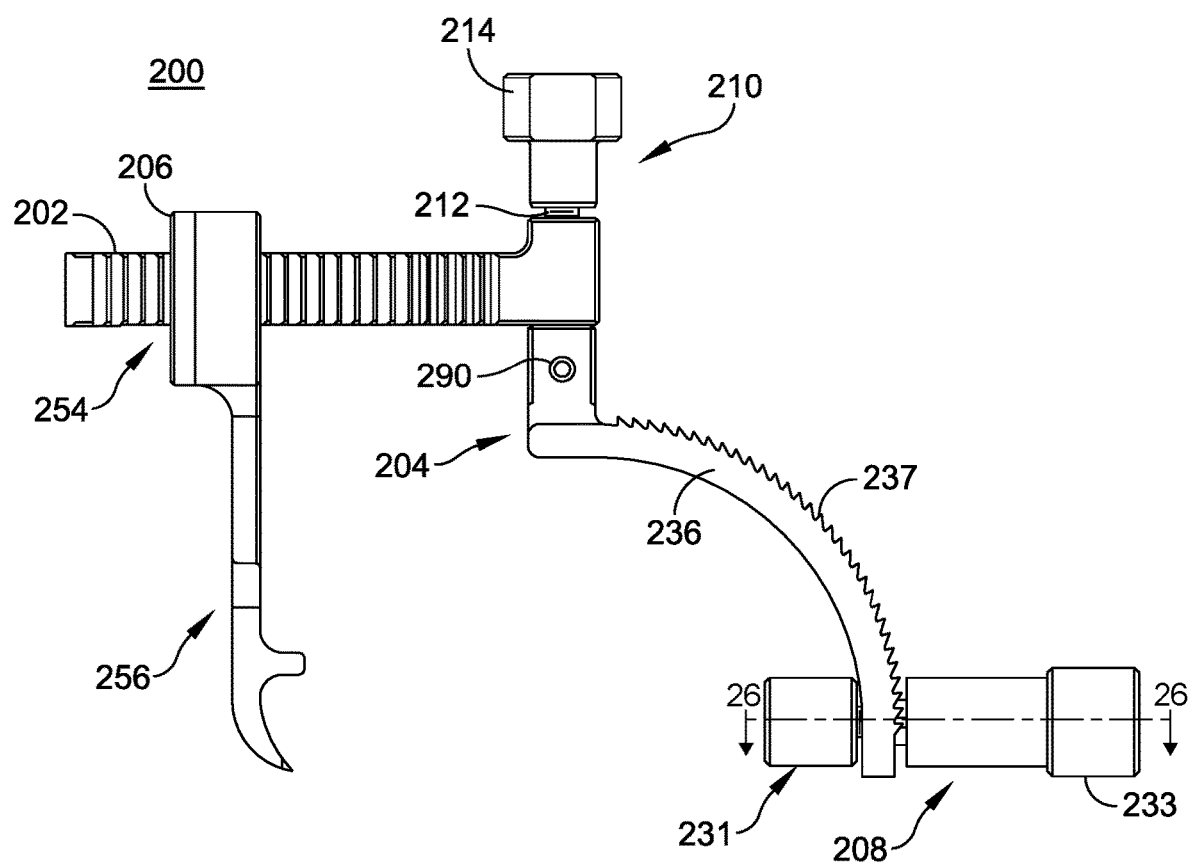
FIG. 24 shows a front view of an apparatus for correcting bone deformities, according to another embodiment.
Figure 25:
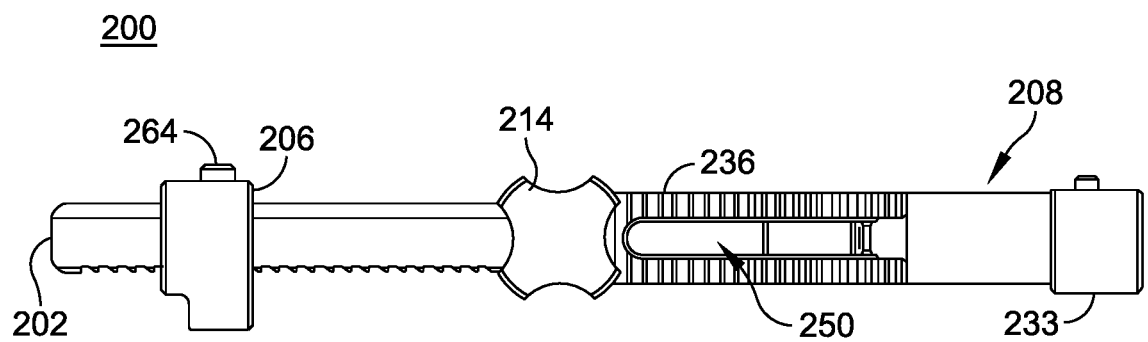
FIG. 25 shows a top view of the apparatus of FIG. 24.
Figure 26:
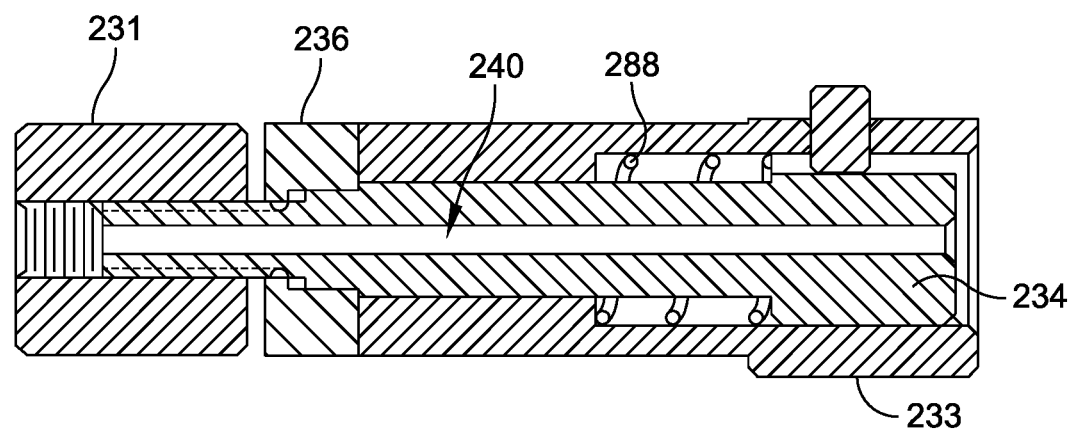
FIG. 26 shows a front cross-sectional view of the apparatus of FIG. 24.

As shown in FIG. 24, the apparatus 200 includes an arcuate portion 236 that is integrally formed with, or fixedly coupled to, the first arm member 204. The rotation guide 208 is slidably coupled to the arcuate portion 236. As shown in the top view of FIG. 25, the arcuate portion includes a slot 250 within which the rotation guide 208 is partially disposed. As shown in FIG. 26, the rotation guide 208 includes a nut 231, a wire retainer 234, and a sleeve 233. The wire retainer 234 includes a bore 240 configured to receive a k-wire. The retainer 234 extends through the slot 250 and engages the nut 231, for example via a threaded connection. The sleeve 233 at least partially surrounds the wire retainer 234 on the side of the arcuate portion 236 opposite the nut 231. The sleeve 233 engages one or more of ratchet teeth 237 (shown in FIG. 25) on the arcuate portion 236 to restrict translation of the rotation guide 208 along the arcuate portion 236. The rotation guide 208 can also include a biasing member 288, such as a spring, biasing the sleeve 233 toward a position in which the sleeve 233 is engaged with the ratchet teeth 237. In order to change the position of the rotation guide 208, the user can pull the sleeve 233 away from the arcuate portion 236 to disengage the sleeve 233 from the ratchet teeth 237.

The apparatus 200 also includes a locking mechanism 210 that includes a knob 214 and a locking post 212. The locking post 212 is threadably coupled to the knob 214 and extends through a bore in the elongated member 202. The locking post 212 is coupled to the first arm member 204 such that the locking post 212 and first arm member 204 rotate together. The locking post 212 and first arm member 204 can be coupled in any appropriate manner. For example, a pin 290 can be used to couple the locking post 212 and first arm member 204, as shown in FIG. 24. The first arm member 204 is able to rotate about arm axis 224 when the locking mechanism 210 is in an unlocked configuration. In order to lock the rotation of the first arm member 204, the user rotates the knob 214 to tighten the first arm member 204 against the elongated member 202. The locking mechanism 210 can be held in the locked configuration by the frictional forces between the threads or, additionally or alternatively, other means of retention such as a pin or ratchet teeth can be used.

Figure 27:
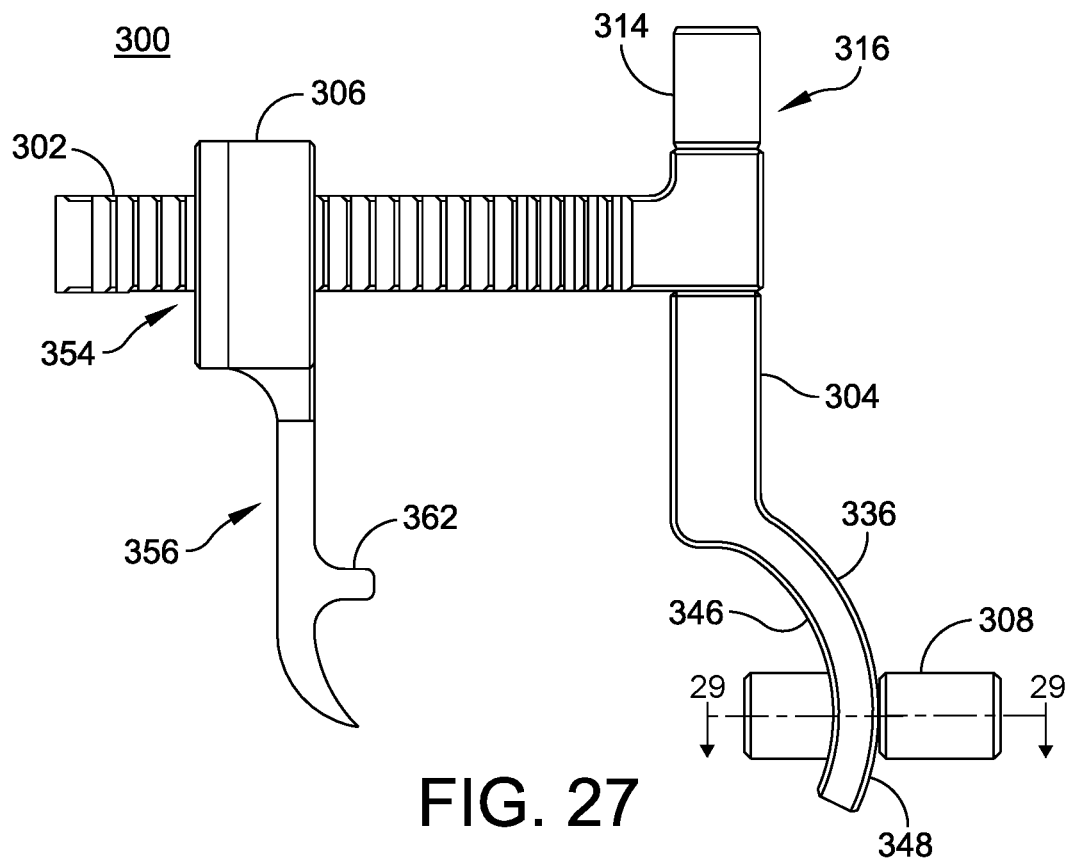
FIG. 27 shows a front view of an apparatus for correcting bone deformities, according to another embodiment.
Figure 28:
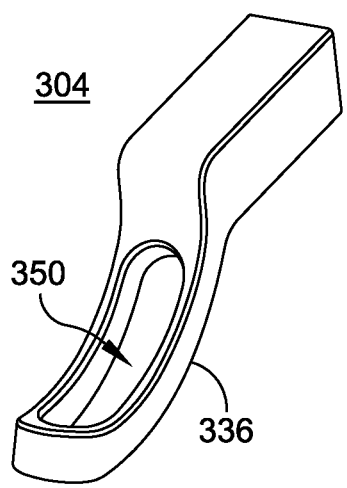
FIG. 28 shows a perspective view of a first arm member of the apparatus of FIG. 27.
Figure 29:
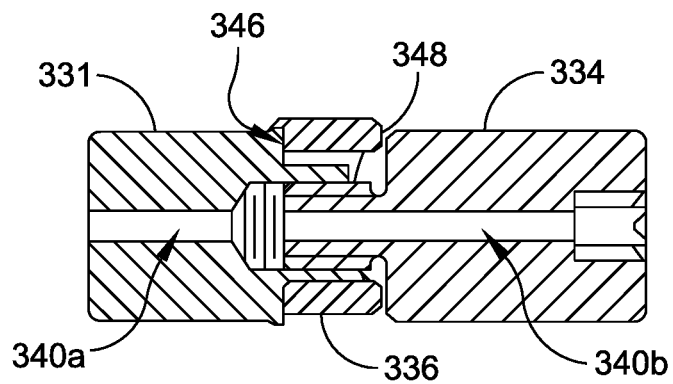
FIG. 29 shows a front cross-sectional view of the apparatus of FIG. 27.

In another embodiment, shown in FIGS. 27-29, an apparatus 300 includes a first arm member 304 and a rotation guide 308. The first arm member 304 includes an arcuate portion 336 defining a slot 350 (shown in FIG. 28). As shown in FIG. 29, the rotation guide 308 includes a nut 331 and a retainer 334. The nut 331 includes a bore 340a and the retainer includes an axially aligned bore 340b. The bores 340a, 340b are configured to receive a k-wire therein. As shown best in the cross-sectional view of FIG. 29, the retainer 334 and nut 331 are threadably engaged and at least one of the retainer 334 and nut 331 extend through the slot 350 of the arcuate portion 336. In order to lock the rotation guide 308 in position, the threaded engagement of the retainer 334 and the nut 331 is tightened (e.g., by clockwise or counterclockwise rotation) to press the nut 331 against the inner face 346 of the arcuate portion 336 and the retainer 334 against the outer face 348 of the arcuate portion 336. The retainer 334 can include a recess for receiving a driving tool to assist with tightening of the retainer 334.

Apparatus 300 includes a locking mechanism 310 to lock rotation of the first arm member 304. The locking mechanism 310 includes a knob 314 and a threaded rod (not shown). The threaded rod is rigidly coupled to the knob 314 and extends through a bore in the elongated member 302. The threaded rod is threadably coupled to the first arm member 304. In order to lock the rotation of the first arm member 304, the user rotates the knob 314 to tighten the first arm member 304 against the elongated member 302.

Figure 36:
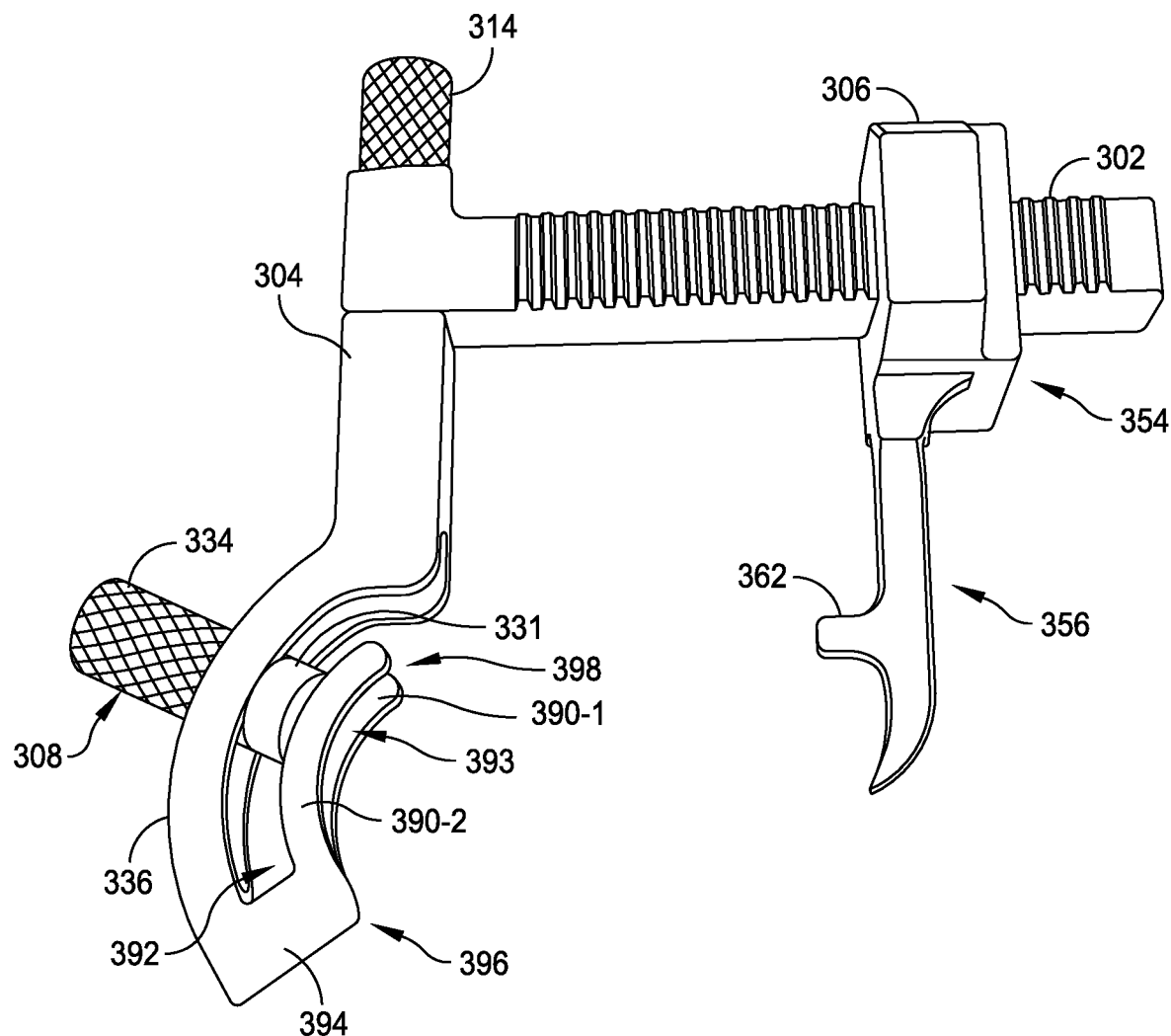
FIG. 36 shows a front perspective view of an apparatus for correcting bone deformities, according to another embodiment described herein.
Figure 37:
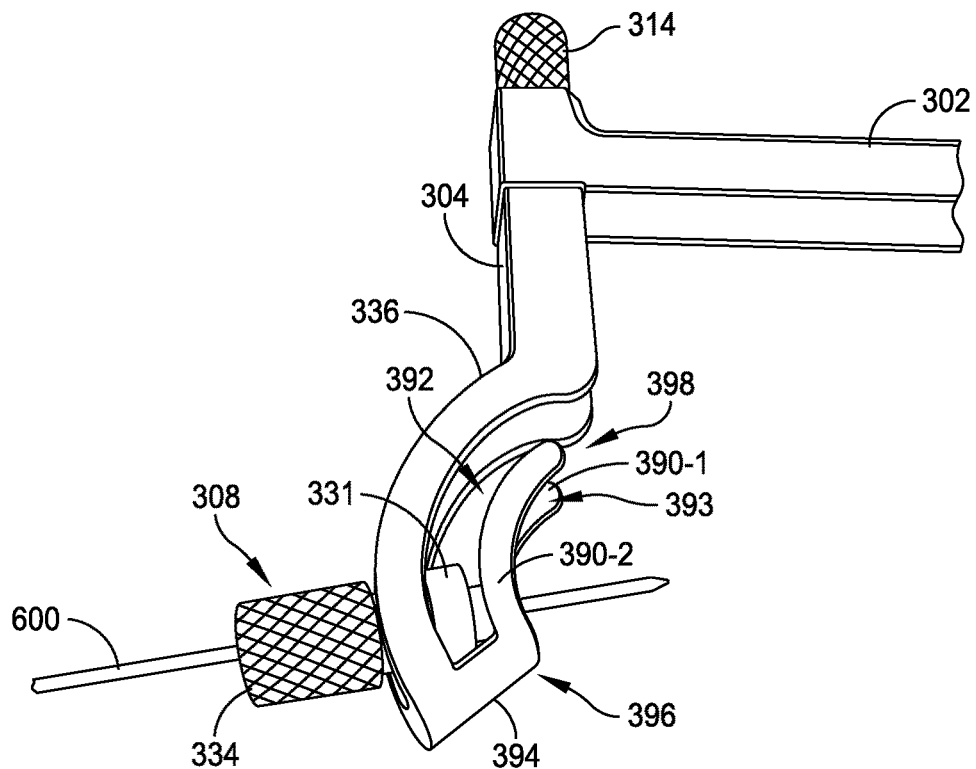
FIG. 37 shows a front perspective view of the first arm member of the apparatus of FIG. 36, with the rotation guide in a first position.
Figure 38:
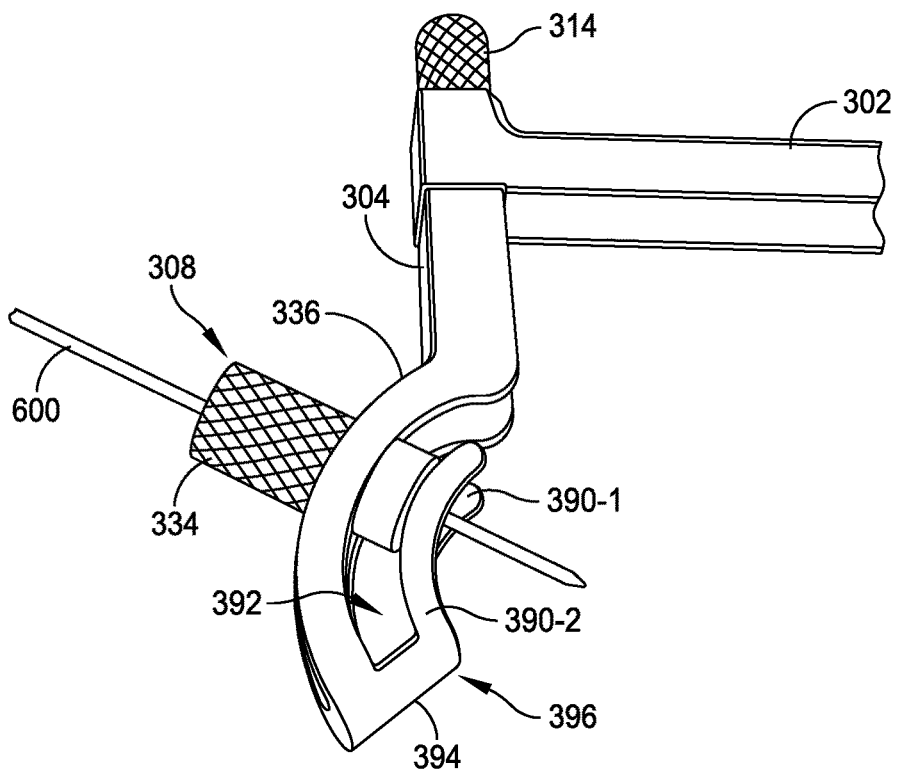
FIG. 38 shows a front perspective view of the first arm member of the apparatus of FIG. 36, with the rotation guide in a second position.

In another embodiment, shown in FIGS. 36-38, the apparatus 300 further includes contact arms 390. The contact arms 390 are positioned such that, when the apparatus 300 is in use, the contact arms 390 are in contact with the patient (e.g., the first metatarsal). While FIGS. 36-38 illustrate a first contact arm 390-1 and a second contact arm 390-2, it should be understood that the apparatus 300 can include only a single contact arm 390 or more than two contact arms 390. A track 392 is defined between the contact arms 390 and the arcuate portion 336. The nut 331 of the rotation guide 308 translates within the track 392 formed between the contact arms 390 and the inner face 346 (shown in FIG. 27) of the arcuate portion 336. As a result, the nut 331 is not in contact with the patient during use. Instead, during rotation of the first metatarsal (e.g. first metatarsal 602 shown in FIG. 31), the bone is in contact with the contact arms 390. This can provide a number of advantages including increasing the surface area of contact between the bone and the first arm member 304 to distribute the force applied to the bone during reduction of the intermetatarsal angle. In various embodiments, the contact arms 390 have a concave inner face to provide a smooth surface for rotation of the bone and to further increase the contact area with the bone. In some embodiments, the contact arms 390 are concentric with the arcuate portion 336

The first contact arm 390-1 and the second contact arm 390-2 define a slot 393 between them to allow passage of a k-wire 600 (shown in FIGS. 37 and 38) or other pin through the bores 340a, 340b (shown in FIG. 29) in the rotation guide 308, through the slot 393, and into a bone, such as the first metatarsal. The k-wire 600 can translate within the slot 393 as the rotation guide 308 is rotated to rotate the bone.

In the embodiment shown in FIGS. 36-38, the contact arms 390 are coupled to the arcuate portion 336 of the first arm member 304. The contact arms 390 can be connected to the arcuate portion 336 by a connecting portion 394 at the end of the arcuate portion 336 away from the elongated member 302. The contact arms 390 extend from a first end 396 coupled to the connecting portion 394 to a second, free end 398 nearer the elongated member 302. Alternatively, in other embodiments (not shown), the contact arms 390 can be coupled to a portion of the first arm member 304 that is nearer the elongated member 302 (i.e., the top of the arcuate portion 336).

FIG. 37 shows the apparatus 300 with the rotation guide 308 in a first position toward the bottom of the arcuate portion 336 and the track 392. This may be approximately the position of the rotation guide 308 prior to rotation of the first metatarsal in the frontal plane (i.e., about a longitudinal axis). FIG. 38 shows the rotation guide 308 in a second position nearer the top of the arcuate portion 336 and track 392. This may be approximately the position of the rotation guide 308 after rotation of the first metatarsal in the frontal plane (i.e., about a longitudinal axis).

It should be understood that other embodiments illustrated herein—such as the apparatus 100 shown in FIG. 1 and the apparatus 200 shown in FIG. 24—can include contact arms such that the rotation guide is spaced apart from the first metatarsal during use. For example, in the embodiment shown in FIG. 1, contact arms may extend from the first arm member 104. In the embodiment shown in FIG. 24, contact arms may extend from first arm member 204 (e.g., from the arcuate portion 236).

Figure 30:
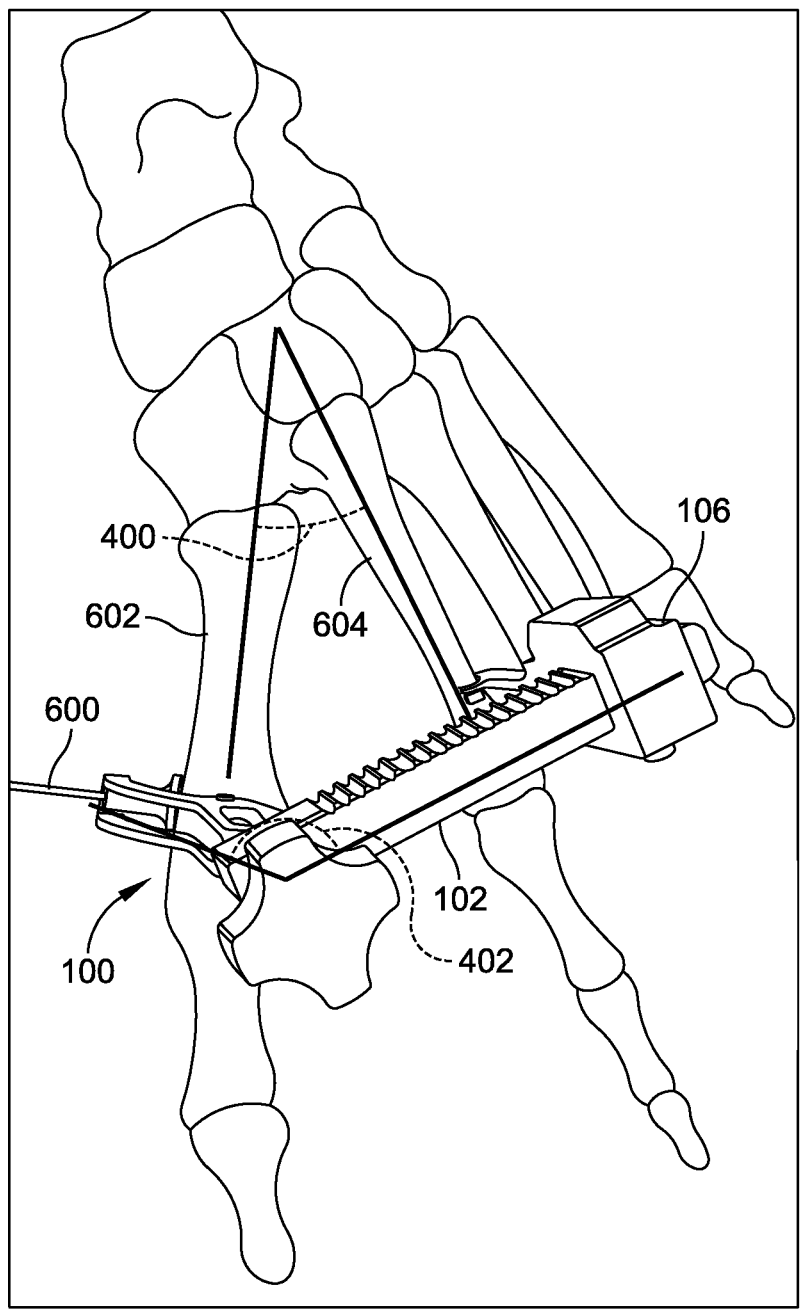
FIG. 30 shows a top view of the apparatus of FIG. 1 in use.

In another aspect, a method of using the apparatuses previously described is provided. The apparatuses can be used in the correction of hallus valgus angle, bunion deformities, and/or an increased intermetatarsal angle. Such an intermetatarsal angle 400 is shown in FIG. 30. Steps of use of the apparatus 100 are shown in FIGS. 31-35. One of skill in the art would appreciate that the other embodiments described herein can be used in a similar fashion.

Figure 31:
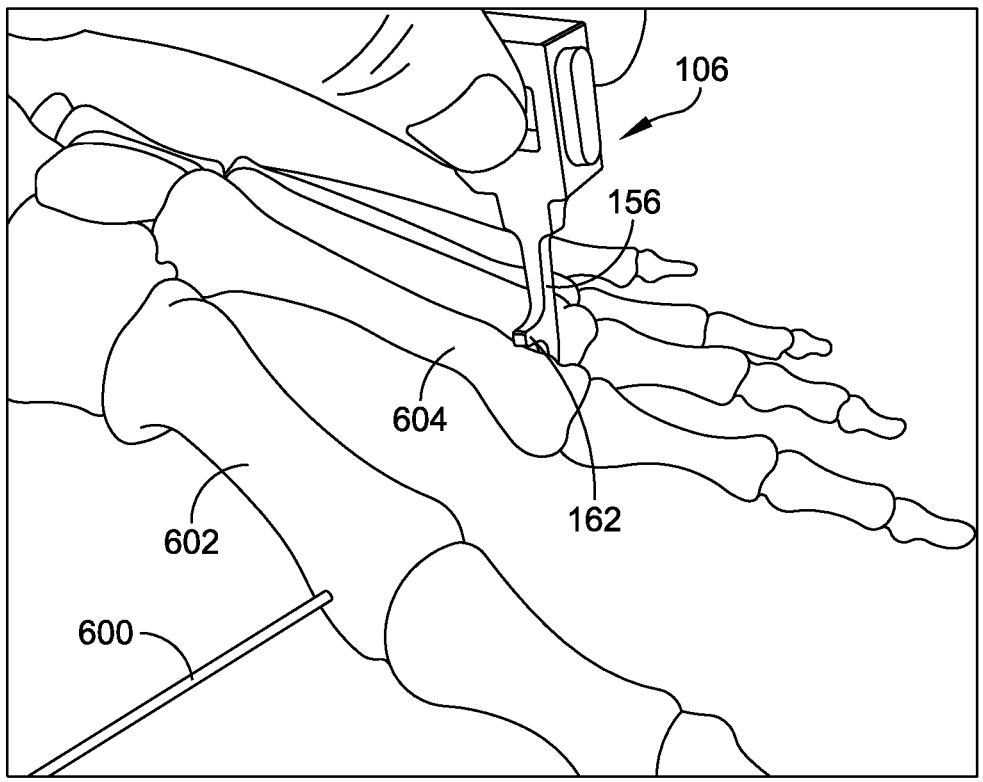
FIG. 31 shows the apparatus of FIG. 1 in a first step of use in which the second arm member is engaged with a second metatarsal.

As shown in FIG. 31, a k-wire 600 is inserted into a first metatarsal 602. In one embodiment, the k-wire 600 is inserted in a medial to lateral orientation. The k-wire 600 can be, for example, inserted into the head of the first metatarsal 602. In one embodiment, the k-wire 600 is inserted orthogonal to a longitudinal axis of the first metatarsal 602.

As also shown in FIG. 31, the extension 156 of the second arm member 106 is brought into engagement with a second metatarsal 604. The concave portion 160 (see FIG. 16) contacts the lateral side of the second metatarsal 604. Further, the protrusion 162 contacts the superior side of the second metatarsal 604 such that the protrusion 162 extends toward the first metatarsal 602.

Figure 32:
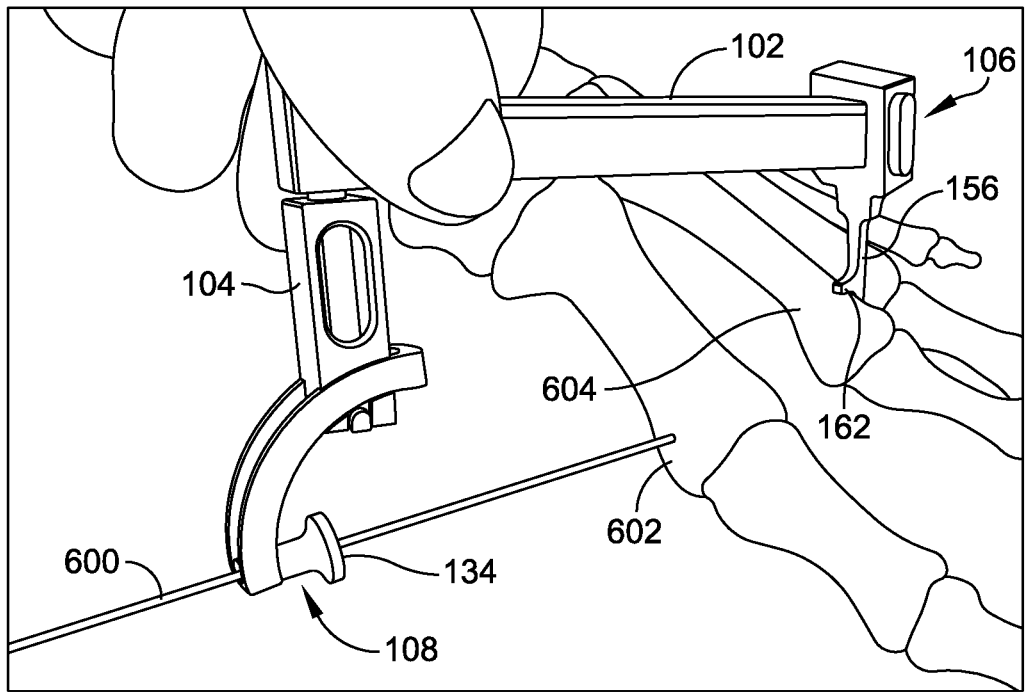
FIG. 32 shows the apparatus of FIG. 1 in a second step of use in which a k-wire is received in the wire retainer.
Figure 33:
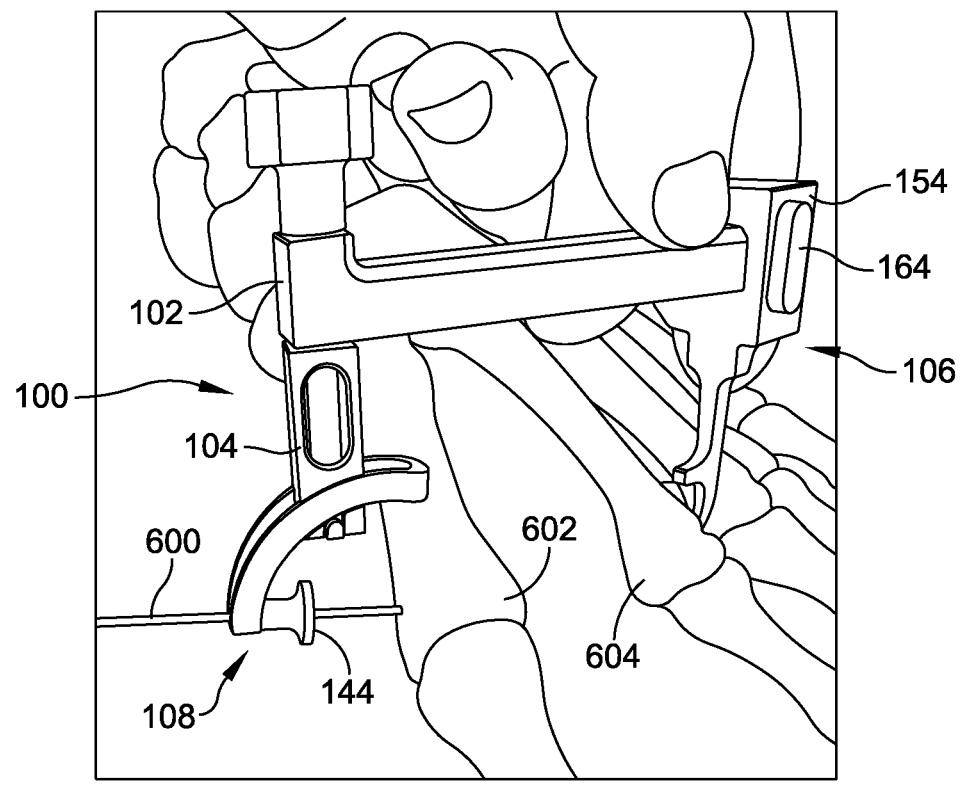
FIG. 33 shows the apparatus of FIG. 1 in a third step of use in which the elongated member is coupled to the second arm member.
Figure 34:
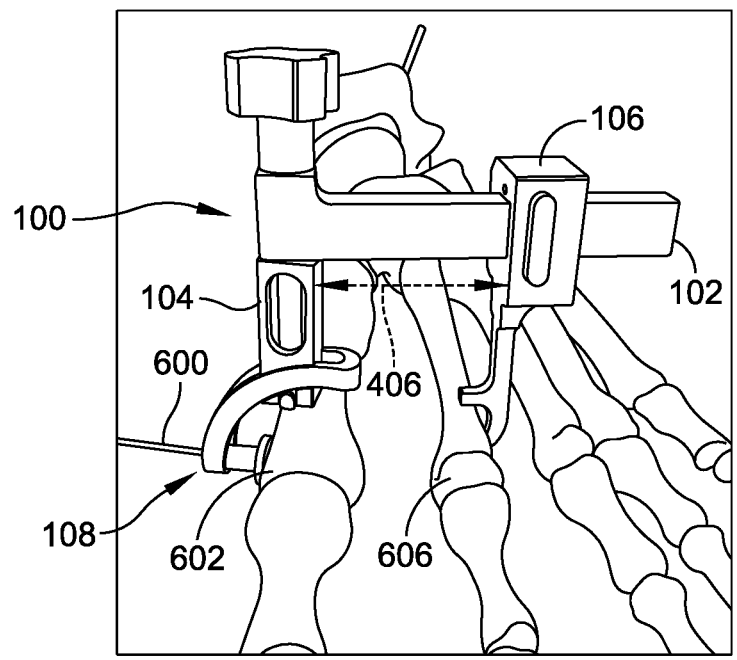
FIG. 34 shows the apparatus of FIG. 1 in a fourth step of use in which the intermetatarsal angle is reduced.

As shown in FIG. 32, the bore 140 (see FIG. 10) of the wire retainer 134 is slid over the k-wire 600 to couple the rotation guide 108 to the first metatarsal 602. Further, as shown in FIGS. 32 and 33, the elongated member 102, coupled to the rotation guide 108 via the first arm member 104, is engaged with the attachment portion 154 of the second arm member 106. The first arm member 104 is brought closer to the second arm member 106 until the bone engagement face 144 of the rotation guide 108 contacts the first metatarsal 602, as shown in FIG. 34. In other embodiments, such as when the apparatus 300 is used, the method can include bringing the contact arms 390 into contact with the first metatarsal 602 with the rotation guide 308 spaced apart from the first metatarsal 602.

Subsequently, a distance 406 between the first arm member 104 and the second arm member 106 is reduced, thereby reducing the distance between the head of the first metatarsal 602 and the second metatarsal 604. This is continued until the desired intermetatarsal angle 400 is achieved. As the intermetatarsal angle 400 is decreased, the first arm member 104 rotates about the arm axis 124 (see FIG. 5) to accommodate the changing angle 402 (see FIG. 30) of the k-wire 600 with respect to the elongated member 102 in the plane orthogonal to the arm axis 124.

With the intermetatarsal angle 400 in the desired position, the rotation guide 108 can be rotated about the rotation axis 152 to rotate the first metatarsal 602 from a first rotational position, shown in FIG. 35A, to a second rotational position, shown in FIG. 35B. Rotation of the rotation guide 108 rotates the first metatarsal 602 substantially around a longitudinal axis of the first metatarsal 602. In other words, the first metatarsal 602 is rotated in the frontal plane. This frontal plane rotation brings the first metatarsal 602 into proper alignment including, for example, by positioning the sesamoids under the metatarsal head. In so doing, the k-wire 600 acts as a lever to rotate the first metatarsal 602. With the first metatarsal 602 in the desired position, the knob 114 can be tightened to restrict rotation of the first arm member 104 and the rotation guide 108. In embodiments, such as those shown in FIGS. 27 and 36, the retainer 334 of the rotation guide 308 can also be tightened to restrict movement of the rotation guide 308 with respect to the arcuate portion 336. It should be understood that the frontal plane rotation of the first metatarsal 602 can be done before, during, or after reduction of the intermetatarsal angle. In some instances, as the intermetatarsal angle is reduced, the geometry of the interfacing faces of the first metatarsal and the cuneiform causes the metatarsal to rotate in the frontal plane (i.e., about the longitudinal axis of the first metatarsal).

Bone screws, plates, or other hardware and implants can then be used to secure the position of the first metatarsal 602, as would be understood by one of skill in the art.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

What is claimed is:

1. An apparatus for correcting bunion deformity, the apparatus comprising:
    an elongated member extending from a first end to a second end and having a bore at the first end;
    a first arm member having an arm axis and coupled to the first end of the elongated member and extending in an orthogonal direction from the elongated member so that the arm axis extends in the orthogonal direction, the first arm member including a bore extending therethrough and having two prongs separated by a gap that each define an arcuate external groove at a distal end;
    a second arm member configured to engage the elongated member such that the second arm member can translate along the elongated member between the first and second ends of the elongated member, the second arm member including an attachment portion configured to translatably engage the elongated member and an extension extending from the attachment portion in the same orthogonal direction as the first arm member, wherein a distal end of the extension is configured to engage a bone during use;
    a rotation guide including an arcuate portion slidingly coupled to the arcuate external grooves at the distal end of the first arm member such that the rotation guide is configured to rotate with respect to the first arm member when slid within the arcuate external grooves, the rotation guide defining a bore having a longitudinal axis and configured to receive a k-wire along the bore's longitudinal axis; and
    a locking mechanism comprising a knob and a locking post, the locking post disposed within the bore of the elongated member and the bore of the first arm member, threadably engaged with the knob, and having two locking tabs extending from the locking post, the two locking tabs disposed between the two prongs,
    wherein rotation of the knob causes the two locking tabs to engage the arcuate portion of the rotation guide to restrain rotation of the rotation guide, and
    wherein rotation of the rotation guide with respect to the first arm member causes the longitudinal axis to rotate about a rotation axis.

2. The apparatus of claim 1, wherein the first arm member extends from a first end to a distal end, the first end being rotatably coupled to the first end of the elongated member, the arm axis extending from the first end to the distal end, and wherein the first arm member is configured to rotate about the arm axis.

3. The apparatus of claim 2, wherein the locking mechanism is configured to selectively restrict rotation of the first arm member about the arm axis.

4. The apparatus of claim 1, wherein the arcuate portion of the rotation guide is configured to rotate with respect to the first arm member.

5. The apparatus of claim 1, wherein the first arm member includes an arcuate slot and the rotation guide is engaged with the arcuate external grooves such that the rotation guide is movable along the arcuate external grooves.

6. The apparatus of claim 5, wherein the arcuate external grooves of the first arm member are adjacent, spaced-apart slots extending along the arcuate portion and a portion of the rotation guide extends through each slot.

7. The apparatus of claim 6, wherein the first arm member further includes at least one contact arm configured to contact a second bone during use, wherein a track is defined between the at least one contact arm and the arcuate portion, and wherein a portion of the rotation guide is disposed within the track and is adapted to translate within the track.

8. The apparatus of claim 7, wherein the at least one contact arm includes a first contact arm and a second contact arm, and wherein a slot is defined between the first contact arm and the second contact arm, the slot configured to allow passage of a k-wire therethrough.

9. The apparatus of claim 5, wherein the first arm member further includes at least one contact arm, wherein the at least one contact arm is configured to contact a second bone during use such that the rotation guide is spaced apart from the second bone.

10. The apparatus of claim 5, wherein the arcuate portion of the first arm member includes a plurality of ratchet teeth and wherein the rotation guide is configured to engage one or more of the plurality of ratchet teeth.

11. The apparatus of claim 1, wherein the distal end of the extension includes a protrusion protruding from the extension toward the second end of the first arm member, the protrusion configured to contact the bone during use.

12. An apparatus for correcting bunion deformity, the apparatus comprising:
    an elongated member extending from a first end to a second end and having a bore at the first end;
    a first arm member having an arm axis and coupled to the first end of the elongated member and extending in an orthogonal direction from the elongated member so that the arm axis extends in an orthogonal direction, the first arm member including a bore extending therethrough and having two prongs separated by a gap that each define a curved external groove at a distal end, the first arm member configured to rotate about an arm axis extending from a first end of the first arm member to a second end of the first arm member;
    a second arm member configured to engage the elongated member such that the second arm member can translate along the elongated member between the first and second ends of the elongated member, the second arm member including an attachment portion configured to translatably engage the elongated member and an extension extending from the attachment portion;
    a rotation guide including an arcuate portion, the arcuate portion engaged with the first arm member such that the rotation guide is configured to rotate with respect to the first arm member about a rotation axis defined by the curved external grooves, the rotation guide defining a bore configured to receive a k-wire; and
    a locking mechanism comprising a knob and a locking post, the locking post disposed within the bore of the elongated member and the bore of the first arm member, threadably engaged with the knob, and having two locking tabs extending from the locking post, the two locking tabs disposed between the two prongs,
    wherein rotation of the knob causes the two locking tabs to engage the arcuate portion of the rotation guide to restrain rotation of the rotation guide, and
    wherein the locking mechanism is configured to selectively restrict rotation of the first arm member about the arm axis and rotation of the rotation guide about the rotation axis.

13. An apparatus for correcting bunion deformity, the apparatus comprising:
   an elongated member extending from a first end to a second end and having a bore at the first end;
   a first arm member coupled to the first end of the elongated member and extending from the elongated member, the first arm member including a bore extending therethrough and having two prongs separated by a gap that each define an arcuate external groove at a distal end, and the first arm member including an arcuate portion defining at least one external slot and at least one contact arm configured to contact a first bone during use;
   a second arm member configured to engage the elongated member such that the second arm member can translate along the elongated member between the first and second ends of the elongated member, the second arm member including an attachment portion configured to translatably engage the elongated member and an extension extending from the attachment portion, wherein a distal end of the extension is configured to engage a second bone during use;
   a rotation guide coupled to the arcuate portion of the first arm member such that the rotation guide is configured to translate along the arcuate portion, the rotation guide defining a bore having a longitudinal axis and configured to receive a k-wire along the bore's longitudinal axis; and
   a locking mechanism comprising a knob and a locking post, the locking post disposed within the bore of the elongated member and the bore of the first arm member, threadably engaged with the knob, and having two locking tabs extending from the locking post, the two locking tabs disposed between the two prongs,
   wherein translation of the rotation guide along the arcuate portion causes the longitudinal axis to rotate about a rotation axis; and
   wherein the rotation guide is spaced apart from the first bone during use.

14. The apparatus of claim 13, wherein the at least one contact arm includes a first contact arm and a second contact arm, and wherein a slot is defined between the first contact arm and the second contact arm, the slot configured to allow passage of a k-wire therethrough.

15. The apparatus of claim 13, wherein a track is defined between the arcuate portion and the at least one contact arm and the rotation guide is at least partially disposed in the track defined by the arcuate portion and the at least one contact arm.

* * * * *